United States Patent [19]

Turner et al.

[11] 4,406,882
[45] Sep. 27, 1983

[54] PHARMACEUTICAL COMPOSITION FOR TREATING DISEASES OF THE ORAL CAVITY

[75] Inventors: John C. Turner, London; Lily Baxendale, Hertfordshire, both of England

[73] Assignee: Biorex Laboratories Limited, England

[21] Appl. No.: 342,706

[22] Filed: Jan. 25, 1982

[30] Foreign Application Priority Data

Feb. 6, 1981 [GB] United Kingdom ............... 8103789

[51] Int. Cl.³ .................... A61K 7/16; A61K 7/22; A61K 7/24
[52] U.S. Cl. .................... 424/49; 424/54; 424/55
[58] Field of Search .................... 424/49–58

[56] References Cited

U.S. PATENT DOCUMENTS 3,944,660 3/1976 Gottfried et al. .................... 424/44

FOREIGN PATENT DOCUMENTS

| 2360918 | 6/1974 | Fed. Rep. of Germany . |
|---|---|---|
| 1306M | 5/1962 | France . |
| 51-41447 | 4/1976 | Japan . |
| 54-26339 | 2/1979 | Japan . |
| 54-117040 | 9/1979 | Japan . |
| 798655 | 7/1958 | United Kingdom . |
| 843132 | 8/1960 | United Kingdom . |
| 843133 | 8/1960 | United Kingdom . |
| 843134 | 8/1960 | United Kingdom . |
| 843135 | 8/1960 | United Kingdom . |
| 843136 | 8/1960 | United Kingdom . |
| 843137 | 8/1960 | United Kingdom . |
| 848066 | 9/1960 | United Kingdom . |
| 1049036 | 11/1966 | United Kingdom . |
| 1124976 | 8/1968 | United Kingdom . |

OTHER PUBLICATIONS

A.D.A. Accepted Dental Therapeutics 38th ed. Sep. 1979, American Dental Assocation Chicago, Ill. (Posl#RK 701 A3), pp. 15–16, 48–50, 249–256, 262–269, 279–280, 339–347.
Tamura et al., Chem. Abstr. 95: 108560h (1981) of Shika Kiso Igakkai Zasshi (1981) 23 (1):1–8, Glycynhrrhetinic Acid Ointment for Stomatitis on Oral Mucosa.
Dedieu et al., Chem. Abstr. 94: 361322 (1981) of Brit 1,567,307 May 14, 1980., Mouthwashes of Ammonium Glycyrrhizinate.
Hashimoto et al., Chem. Abstr. 92: 116267n (1980) of Jpn. Kokai Tokkyo Koho 79-117040 Glycyrrhetic Acid Monoammonium Salt in Dentifrices.
Sato et al., Chem. Abstr. 91: 9357h 1979 of Jpn. Kokai Tokkyo Koho 79 26339 Glycyrrhizic Acid or Salts, Di-K Glycyrrhizate in Dentifrices.
Edgar et al., Chem. Abstr. 89: 141063x (1978) of J. Dent Res. (1978) 57 (1): 59–64 Reduction in Enamel Dissolution by Licorice and Glycyrrhizinic Acid.
Takahashi et al., Chem. Abstr. 86: 8582n (1977) of Japan Kokai 7641447 Stearyl Glycyrrhetinate in Dentifrices.
Beriou Chem. Abstr. 84: 49819x (1976) of Brit. 1,393,498 Ammonium Glycyrrhizate in Toothpaste.
Villette Chem. Abstr. 83: 65467r (1975) of Fr. Demande 2225146 Ammonium Glycyrrhizate in Dentifrice.
Veyron et al., Chem. Abstr. 76: 158370Z (1972) of Fr. CAM 222 Addn. to Fr. M 1306 Bucco Dental Inflammatory Disorders Treated with Dentifrices, Elixir sets of β-Glycyrrhetinic Acid.
Simson Chem. Abstr. 69: 99406w (1968) of Brit. 1,124,976 Mouth Ulcers Treated with DI-NA Glycyrrhetinic Acid Hemisuccinate.

*Primary Examiner*—Shep K. Rose
*Attorney, Agent, or Firm*—Wenderoth, Lind & Ponack

[57] ABSTRACT

The present invention provides a water-soluble or water-dispersible particulate pharmaceutical composition comprising, per one part by weight of glycyrrhetinic acid and/or glycyrrhetinic acid derivative (as hereinbefore defined), 10 to 100 parts by weight of lactose and/or sorbitol, 10 to 50 parts by weight of at least one buffer selected from sodium citrate, potassium citrate, sodium tartrate, potassium tartrate, sodium malate and potassium malate and 0.1 to 10 parts by weight of disodium edetate.

6 Claims, No Drawings

PHARMACEUTICAL COMPOSITION FOR TREATING DISEASES OF THE ORAL CAVITY

BACKGROUND OF THE INVENTION

It is well known that certain derivatives of glycyrrhetinic acid, such as the disodium salt of the hemisuccinate of glycyrrhetinic acid, have an excellent anti-inflammatory action and are useful for the treatment of gastric and duodenal ulcers, as well as for the treatment of reflux oesophagitis.

Non-liquid pharmaceutical compositions are also known which comprise at least one hydrophilic colloid and the disodium salt of the hemisuccinate of glycyrrhetinic acid. These compositions adhere well to moist mucous membranes and have been found to be useful for the treatment of ulcerations of the oral cavity. However, the use of these compositions is restricted to cases in which the degree of ulceration is limited and in which the ulcerations are readily accessible. Furthermore, these compositions cannot be used for the treatment of generalized inflammation of the oral cavity, such as stomatitis, which may involve the buccal and labial mucosa, palate, tongue, floor of the mouth and gingivae.

Unfortunately, there are many common and widely spread inflammatory and ulcerative conditions of the oral cavity, including erosive lichen planus, recurrent ulceration of the aphtus and benign mucous membrane pemphigoid types and primary herpetic stomatitis, for which hitherto there has been no satisfactory treatment. Occasionally, in severe cases of primary herpetic stomatitis in immunologically suppressed patients, use has been made of a mouthwash containing idoxuridine but there is a natural reluctance to use this radiomimetic drug.

Consequently, it is an object of the present invention to provide a pharmaceutical composition which is to be used for making a mouthwash for the treatment of the above-mentioned diseases of the oral cavity and for prophylactic purposes in immunologically suppressed patients.

SUMMARY OF THE INVENTION

According to the present invention, there is provided a water-soluble or water-dispersible particulate and preferably granulated pharmaceutical composition comprising, per one part by weight of glycyrrhetinic acid and/or of a glycyrrhetinic acid derivative, as hereinafter defined, 10 to 100 and preferably 30 to 80 parts by weight of lactose and/or sorbitol, 10 to 50 and preferably 15 to 25 parts by weight of at least one buffer selected from sodium citrate, potassium citrate, sodium tartrate, potassium tartrate, sodium malate and potassium malate and 0.1 to 10 parts and preferably 0.3 to 1 part by weight of disodium edetate and optionally comprising a coloring and/or flavoring material.

DETAILED DESCRIPTION OF THE INVENTION

The selection of the constituent components of the new pharmaceutical compositions of the present invention is of paramount importance. Bulking agents which are conventionally used in tablet manufacture, such as starch and the like, would clearly be unsuitable because they are insoluble or substantially insoluble in water and thus could not be used for making up an aqueous solution for use as a mouthwash. The use of mono- and disaccharides, such as glucose and sucrose, which are also commonly used in tablet manufacture, is also contraindicated because of the known cariogenic activity of such materials. Most of the other known water-soluble and low molecular weight saccharides which might, in principle, be considered cannot be used because they are not readily available and/or are too expensive. Consequently, sorbitol and lactose are the only materials which satisfy the essential criteria of being water-soluble, readily available at an economic price and having a very low cariogenic activity.

As is known, freshly secreted saliva is neutral or very nearly so and is also well buffered. It is also known that any marked shift from neutrality can result in the precipitation from solution of many potentially useful glycyrrhetinic acid derivatives, such as the disodium salt of the hemisuccinate thereof. Consequently, it is necessary to incorporate a buffer in the pharmaceutical composition of the present invention which not only ensures a substantially neutral pH but is also compatible with the other components, does not possess an unpleasant taste or leave an unpleasant aftertaste, has a very low toxicity and possesses a high degree of physiological and pharmacological compatibility. Of the large number of buffer substances which might be considered for this purpose, we have found that the only ones which optimally satisfy all the above-mentioned essential criteria are sodium and potassium citrate, sodium and potassium tartrate and sodium and potassium malate.

Glycyrrhetinic acid and many of its useful derivatives form insoluble or substantially insoluble magnesium and calcium salts. However, as is well known, tap water contains variable amounts of magnesium and/or calcium salts. Consequently, it is essential for the pharmaceutical composition of the present invention to contain a component which is not only capable of forming a water-soluble complex or chelate with magnesium and calcium ions but is also physiologically and pharmacologically compatible. We have found that only disodium edetate amply fulfils all these essential criteria.

Apart from glycyrrhetinic acid per se, the pharmaceutical composition of the present invention may also contain one or more derivatives thereof, such as the 3-0-acyl derivatives and especially those in which the acyl radical contains a carboxyl group (see our British Pat. Nos. 843,133 and 1,387,499), esters of glycyrrhetinic acid and of 3-0-acyl derivatives of glycyrrhetinic acid (see our British Pat. No. 1,255,672) and also 2-($\omega$-carboxyalkanoyl (and cycloalkanoyl)oxymethyl)-glycyrrhetinic acid derivatives (see our British Pat. No. 1,476,053). In those cases where use is made of a glycyrrhetinic acid derivative containing one or more free carboxyl groups, such groups are preferably salified and used, for example, in the form of alkali metal salts, the sodium salts being especially preferred. Of the large number of glycyrrhetinic acid derivatives which can be used, the preferred ones include the disodium salt of glycyrrhetinic acid hemisuccinate, the disodium salt of mono-(glycyrrhet-3-yl)-cis-cyclohexane-1,2-dicarboxylic acid and cinnamyl glycyrrhetate.

Although the glycyrrhetinic acid derivatives used according to the present invention are known to possess anti-inflammatory properties, it is surprising that they also exert a dramatic healing action when used in a mouthwash, in which the contact time is very limited, for the treatment of hitherto intractable diseases, such as erosive lichen planus, pemphigoid types of ulceration, herpetic stomatitis and aphthous ulcers.

In order to improve the patient acceptability of the pharmaceutical compositions according to the present invention, it is desirable to add an appropriate coloring and/or flavoring material. We have found that peppermint is the most widely acceptable flavoring for the compositions according to the present invention but other flavorings may, of course, also be used. Furthermore, we have also found that the most widely acceptable coloring for the compositions according to the present invention is green. This can be obtained, for example, by admixing appropriate chlorophyllins or permicol lime green. However, it is to be understood that any pharmaceutically acceptable coloring material may be used.

We have found that 30 ml. is an adequate volume for a single mouthwash and that approximately 2 g. of the pharmaceutical composition of the present invention is sufficient to provide the desired effect. Consequently, for ease of use, the composition is preferably packed in individual sealed sachets, each of which contains 2 g. of composition, a plurality of such sachets being packed in a larger container in order to provide an adequate course of treatment for a patient.

In order to obtain the desired effect, it is recommended that the patient cleans the mouth after breakfast, luncheon and before retiring at night and then swishes the mouthwash around the mouth for about 30 seconds, after which the mouthwash is spat out. It is recommended that, in order to obtain the maximum beneficial effect, no food or drink is consumed for at least 30 minutes after using the mouthwash.

The following Examples are given for the purpose of illustrating the present invention:

EXAMPLE 1

| Components: | |
|---|---|
| disodium salt of glycyrrhetinic acid hemisuccinate | 2.0 g. |
| granulated sodium citrate | 40.0 g. |
| disodium edetate | 1.0 g. |
| spray-dried lactose | 156.15 g. |
| peppermint oil | 0.8 g. |
| sodium copper chlorophyllin | 0.05 g. |
| purified water | 20 ml. |
| diethyl ether | 4 ml. |

The disodium salt of glycyrrhetinic acid hemisuccinate and the disodium edetate are thoroughly mixed, followed by admixing the sodium citrate and then the lactose. The sodium copper chlorophyllin is dissolved in the 20 ml. of purified water and added to the mixture which is then granulated in a pestle and passed through a 16 mesh sieve. After drying overnight at 50° C., the peppermint oil dissolved in the diethyl ether is added thereto and thoroughly mixed therewith, whereafter the diethyl ether is allowed to evaporate.

2 g. of the granules thus obtained, when dissolved in 30 ml. of water, give a clear blue-green solution with a pH of 7.4.

A similar product is obtained when an equivalent amount of the disodium salt of mono-(glycyrrhet-3-yl)-cis-cyclohexane-1,2-dicarboxylic acid or of cinnamyl glycyrrhetate is used instead of the disodium salt of glycyrrhetinic acid hemisuccinate.

EXAMPLE 2

| Components: | |
|---|---|
| disodium salt of glycyrrhetinic acid hemisuccinate | 0.150 kg. |
| lactose | 11.707 kg. |
| sodium citrate | 3.000 kg. |
| disodium edetate | 0.075 kg. |
| peppermint oil | 0.060 kg. |
| permicol lime green coloring | 0.0075 kg. |
| purified water | |

The disodium salt of glycyrrhetinic acid hemisuccinate and the disodium edetate are mixed together and then the sodium citrate is admixed. The mixture thus obtained is transferred to a Hobart mixer and the lactose is added, followed by mixing for 30 minutes at a low speed.

The coloring material is dissolved in about 1 liter of purified water and added slowly to the mixture, followed by about 0.5 liters of purified water, a stiff, uniformly colored paste being obtained, which is granulated through a size 16 mesh sieve on an oscillating granulator, the granules obtained being dried overnight at 50° C.

The dried granules are then passed through a 16 mesh sieve and the peppermint oil slowly added, with stirring, until a uniform mixture is obtained. The final granulate thus obtained is then stored in an air-tight container.

EXAMPLE 3

| Components: | |
|---|---|
| disodium salt of mono-(glycyrrhet-3-yl)-cis-cyclohexane-1,2-dicarboxylic acid | 2.2 g. |
| granulated potassium citrate | 41.0 g. |
| disodium edetate | 1.0 g. |
| sorbitol | 83.1 g. |
| peppermint oil | 0.8 g. |
| sodium copper chlorophyllin | 0.05 g. |
| purified water | 20 ml. |
| diethyl ether | 4 ml. |

The components are worked up to give a granulate in the manner described in Example 1.

EXAMPLE 4

| Components: | |
|---|---|
| cinnamyl glycyrrhetate | 2.2 g. |
| sodium tartrate | 40.0 g. |
| disodium edetate | 1.0 g. |
| lactose | 140.0 g. |
| peppermint oil | 0.8 g. |
| permicol lime green coloring | 0.08 g. |
| purified water | 20 ml. |
| diethyl ether | 4 ml. |

The components are worked up to give a granulate in the manner described in Example 1.

EXAMPLE 5

| Components: | |
|---|---|
| disodium salt of glycyrrhetinic acid hemisuccinate | 2.0 g. |
| potassium malate | 32.0 g. |
| disodium edetate | 1.0 g. |
| sorbitol | 92.0 g. |
| peppermint oil | 0.8 g. |

-continued

| Components: | |
|---|---|
| sodium copper chlorophyllin | 0.05 g. |
| purified water | 20 ml. |
| diethyl ether | 4 ml. |

The components are worked up to give a granulate in the manner described in Example 1.

The following Table summarizes the results obtained in a limited clinical trial using two different glycyrrhetinic acid derivatives, namely, Viroxolone (the disodium salt of glycyrrhetinic acid hemisuccinate) and Biociclone (the disodium salt of mono-(glycyrrhet-3-yl)-cis-cyclohexane-1,2-dicarboxylic acid). Other clinical trials which have been carried out clearly demonstrated that the mouthwash compositions according to the present invention bring about a dramatic healing and resolution of diseases of the oral cavity which have hitherto proved to be intractable. Thus, it has been demonstrated clinically that the pain and fever frequently associated with herpetic diseases of the oral cavity often disappear within the course of 24 to 48 hours, after which time visual manifestations of the diseases (lesions) are often no longer apparent.

TABLE

| preparation | clinical status | number of patients | results |
|---|---|---|---|
| Viroxolone mouthwash | aphthous ulcer | 12 | 10/12 pain reduced |
| | | | 1/12 no improvement |
| | | | 1/12 complete recurrence |
| | | | 1/12 coelic disease (recurred) |
| | | | 4/12 ulcers healed completely |
| | | | 1/12 pain-free but ulcers persisted |
| Biociclone mouthwash | aphthous ulcer | 7 | 7/7 pain reduced |
| | | | 7/7 ulcers healed |
| | | | 1/7 herpetic origin |
| | | | 2/7 recurred |
| | | | 1/7 coeliac disease (recurred) |
| | | | 2/7 no recurrence with maintenance of treatment |
| | | | 1/7 recurrence even with maintenance of treatment |
| Viroxolone mouthwash | chronic erosive lichen planus | 7 | 1/7 less painful lesions, resolved on maintenance of therapy |
| | | | 3/7 mouth more comfortable, lesions unchanged |
| | | | 1/7 pain-free in 1 week, lesions improved |
| | | | 1/7 mouth possibly less uncomfortable, lesions unchanged |
| | | | 1/7 pain became more severe, withdrew |
| Viroxolone mouthwash | acute radiation mucositis | 1 | more comfortable in 48 hrs., resolved painlessly in 3 weeks |

We claim:

1. A water-soluble or water-dispersible particulate composition comprising:
   per one part by weight of at least one glycyrrhetinic acid derivative selected from the group consisting of glycyrrhetinic acid hemiesters and the salts thereof and the esters of glycyrrhetinic acid and of 3-0-acyl derivatives of glycyrrhetinic acid, 10 to 100 parts by weight of at least one compound selected from the group consisting of lactose and sorbitol, 10 to 50 parts by weight of at least one buffer selected from the group consisting of sodium citrate, potassium citrate, sodium tartrate, potassium tartrate, sodium malate and potassium malate and 0.1 to 10 parts by weight of disodium edetate.

2. A pharmaceutical composition according to claim 1, comprising:
   per one part by weight of glycyrrhetinic acid derivative, 30 to 80 parts by weight of at least one compound selected from the group consisting of lactose and sorbitol, 15 to 25 parts by weight of buffer and 0.3 to 1 part by weight of disodium edetate.

3. A pharmaceutical composition according to claim 1, which additionally comprises at least one member from the group consisting of coloring materials and flavoring materials.

4. A pharmaceutical composition according to claim 1, wherein the glycyrrhetinic acid derivative is the disodium salt of glycyrrhetinic acid hemisuccinate, the disodium salt of mono-(glycyrrhet-3-yl)-cis-cyclohexane-1,2-dicarboxylic acid or cinnamyl glycyrrhetate.

5. A method of treating or preventing inflammatory and ulcerative diseases of the oral cavity in humans, which comprises washing the mouth of a human with an aqueous solution or dispersion of a pharmaceutical composition comprising:
   per one part by weight of at least one glycyrrhetinic acid derivative selected from the group consisting of glycyrrhetinic acid hemiesters and the salts thereof and the esters of glycyrrhetinic acid and 3-0-acyl derivatives of glycyrrhetinic acid, 10 to 100 parts by weight of at least one compound selected from the group consisting of lactose and sorbitol, 10 to 50 parts by weight of at least one buffer selected from the group consisting of sodium citrate, potassium citrate, sodium tartrate, potassium tartrate, sodium malate and potassium malate and 0.1 to 10 parts by weight of disodium edetate.

6. A method according to claim 5, which comprises washing the mouth with a mouthwash prepared by dissolving or suspending 2 g. of a pharmaceutical composition comprising:
   per one part by weight of at least one glycyrrhetinic acid derivative selected from the group consisting of glycyrrhetinic acid hemiesters and the salts thereof and the esters of glycyrrhetinic acid and 3-0-acyl derivatives of glycyrrhetinic acid, 10 to 100 parts by weight of at least one compound selected from the group consisting of lactose and sorbitol, 10 to 50 parts by weight of at least one buffer selected from the group consisting of sodium citrate, potassium citrate, sodium tartrate, potassium tartrate, sodium malate and potassium malate and 0.1 to 10 parts by weight of disodium edetate, in 30 ml. of water.

* * * * *